(12) United States Patent
Zhou et al.

(10) Patent No.: US 10,793,619 B2
(45) Date of Patent: Oct. 6, 2020

(54) PREPARATION AND SELECTION OF CELLS FOR PRODUCING BISPECIFIC ANTIBODIES

(71) Applicant: Wuhan YZY Biopharma Co., Ltd., Wuhan (CN)

(72) Inventors: Pengfei Zhou, Wuhan (CN); Jing Zhang, Wuhan (CN); Rui Wang, Wuhan (CN); Xiang Zhou, Wuhan (CN); Xiaoyan Liu, Wuhan (CN); Lingli Hu, Wuhan (CN); Sisi Fu, Wuhan (CN); Hui Zhong, Wuhan (CN)

(73) Assignee: Wuhan YZY Biopharma Co., Ltd., Wuhan (CN)

( * ) Notice: Subject to any disclaimer, the term of this patent is extended or adjusted under 35 U.S.C. 154(b) by 575 days.

(21) Appl. No.: 15/315,997

(22) PCT Filed: Jun. 5, 2014

(86) PCT No.: PCT/CN2014/079303
§ 371 (c)(1),
(2) Date: Dec. 2, 2016

(87) PCT Pub. No.: WO2015/184626
PCT Pub. Date: Dec. 10, 2015

(65) Prior Publication Data
US 2017/0088604 A1    Mar. 30, 2017

(51) Int. Cl.
*G01N 31/00*    (2006.01)
*G01N 33/53*    (2006.01)
*C07K 16/00*    (2006.01)
*G01N 33/68*    (2006.01)

(52) U.S. Cl.
CPC ......... *C07K 16/00* (2013.01); *G01N 33/6854* (2013.01); *C07K 2317/31* (2013.01)

(58) Field of Classification Search
None
See application file for complete search history.

(56) References Cited

U.S. PATENT DOCUMENTS 9,079,965 B2 * 7/2015 Zhou ...................... C07K 16/32

FOREIGN PATENT DOCUMENTS

| CN | 1545621 A | 11/2004 |
|---|---|---|
| CN | 1328157 C | 7/2007 |
| CN | 101472947 A | 7/2009 |
| CN | 102369215 A | 3/2012 |
| CN | 103097542 A | 5/2013 |
| WO | WO2014079000 A1 | 5/2014 |

OTHER PUBLICATIONS

Zuo et al. (Protein Engineering, vol. 13, No. 5, pp. 361-367, 2000).*
Luo et al. (Luo et al. Moleuclar Pharmaceutics, 2014, vol. 11, pp. 1750-1761).*
Costa et al. (European Journal of Pharmaceutics and Biopharmaceutics 74 (2010) 127-138).*
Zuo et al. (Protein Engineering, vol. 13, No. 5, pp. 361-367, 2000) (Year: 2000).*
Luo et al. (Luo et al. Moleuclar Pharmaceutics, 2014, vol. 11, pp. 1750-1761) (Year: 2014).*
Costa etal. (European Journal of Pharmaceutics and Biopharmaceutics 74 (2010) 127-138). (Year: 2010).*
International Search Report for PCT/CN2014/079303 filed Jun. 5, 2014 dated Mar. 16, 2015 (3 pages).
Zuo et al., "An efficient route to the production of an IgG-like bispecific antibody," Protein Engineering vol. 13, No. 5, pp. 361-367 (2000).
Grosjean et al., "S-phase synchronized CHO cells show elevated transfection efficiency and expression using CaPi," Cytotechnology, vol. 38, pp. 57-62 (2002).
Zhuang Zuo et al. An Efficient Route to the Production of an IgG-like Bispecific Antibody, Protein Engineering, vol. 13 No. 5 pp. 361-367, 2000. Department of Molecular and Cell Biology, ImClone System Incorporated, New York, NY, USA.
Frederic Grosjean et al. S-phase synchronized CHO cells show elevated transfection efficiency and expression using CaPi, Cytotechnology 38: 57-62, 2002. Kluwer Academic Publisher, Netherlands.

* cited by examiner

*Primary Examiner* — Lisa V Cook
(74) *Attorney, Agent, or Firm* — Sheppard Mullin Richter & Hampton LLP

(57) ABSTRACT

Provided are compositions and methods for preparing a cell suitable for producing a bispecific antibody. A plurality of eukaryotic cells are incubated with an agent under conditions to allow the cells to arrest at G1/S phase. The agent is then removed from the cells and the cells are transfected with a first vector comprising a sequence encoding a first monovalent antigen-binding unit having specificity to a first antigen and a second vector comprising a sequence encoding a second monovalent antigen-binding unit having specificity to a second antigen. A cell is identified from the plurality of cells that expresses both the first and the second antigen-binding units.

6 Claims, 8 Drawing Sheets

Timeline of conventional mAb cell line development : ~180 days
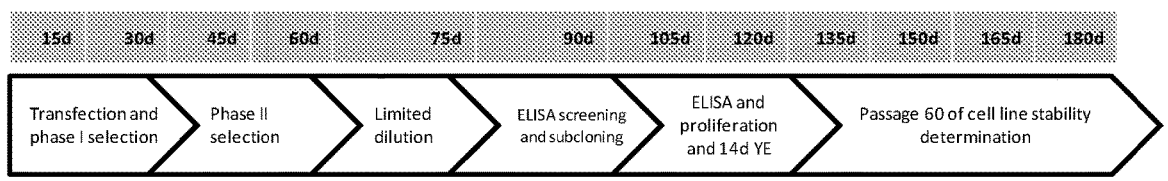
Timeline of the present BiAb cell line development: ~100 days
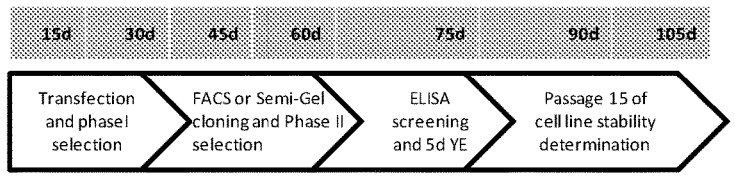
FIG. 1
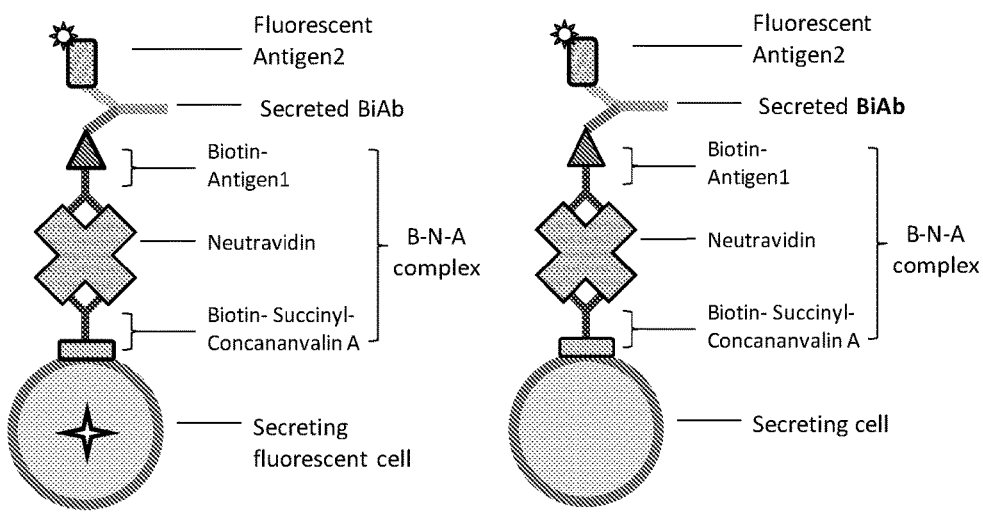
FIG. 2          FIG. 3

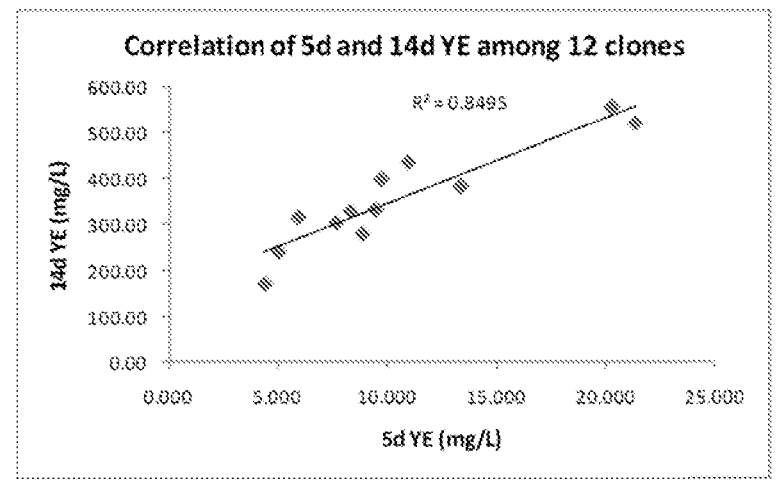
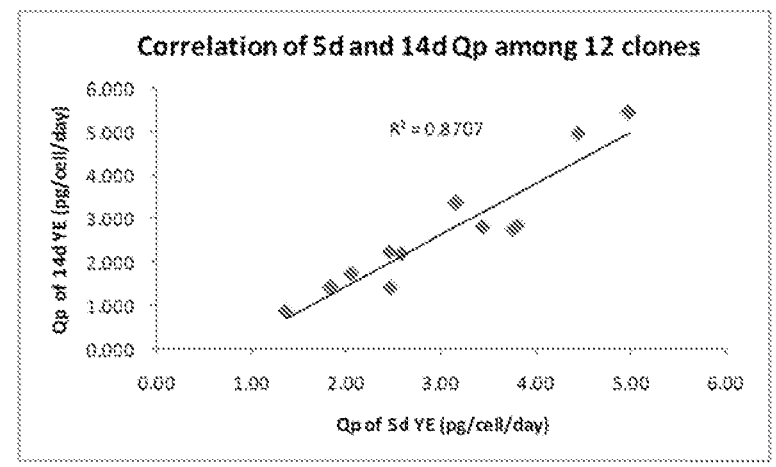
FIG. 14

PREPARATION AND SELECTION OF CELLS FOR PRODUCING BISPECIFIC ANTIBODIES

CROSS REFERENCE TO RELATED APPLICATIONS

This application is a U.S. National Stage Application under 35 U.S.C. § 371 of PCT Application No. PCT/CN2014/079303, filed Jun. 5, 2014, which is incorporated by reference herein for all purposes.

TECHNICAL FIELD

This disclosure is directed to compositions and methods related to generation and selection of cells suitable for producing bispecific antibodies.

BACKGROUND ART

Efficient production of therapeutic protein products, such as antibodies, requires the development and identification of cell lines suitable for such production. Cell line development has undergone several advances over the years, in particular to meet the requirement to cut the time and costs associated with using such complex hosts as production platforms. Advances have been made in the development of cell lines and the cell engineering approach that can be employed to enhance productivity, improve cellular metabolism, control proliferation and apoptosis, and reduce instability.

Production of antibodies presents unique challenges, given antibodies' relatively large size and complex post-translational modifications. Bispecific antibodies, in particular those that include two separate binding units that require expression of both units in a single cell, are even more difficult to produce.

DISCLOSURE OF INVENTION

Technical Problem

The present disclosure, in one embodiment, provides compositions and methods for preparing a cell suitable for producing a bispecific antibody. In one aspect, a plurality of eukaryotic cells are incubated with an agent under conditions to allow the cells to arrest at G1/S phase. The agent can then be removed from the cells and the cells can be transfected with a first vector comprising a sequence encoding a first monovalent antigen-binding unit having specificity to a first antigen and a second vector comprising a sequence encoding a second monovalent antigen-binding unit having specificity to a second antigen. A cell can then be identified from the plurality of cells that expresses both the first and the second antigen-binding units.

Solution to Problem

Technical Solution

In one embodiment, a method is provided for preparing a cell suitable for producing a bispecific antibody, the method comprising: (a) incubating a plurality of eukaryotic cells with an agent under conditions to allow the cells to arrest at G1/S phase; (b) removing the agent from the cells; (c) transfecting the cells with a first vector comprising a sequence encoding a first monovalent antigen-binding unit having specificity to a first antigen and a second vector comprising a sequence encoding a second monovalent antigen-binding unit having specificity to a second antigen; and (d) identifying a cell from the plurality of cells that expresses both the first and the second antigen-binding units. In some aspects, the agent is thymidine.

In some aspects, the first or second vector further comprises a sequence encoding a fluorescent protein.

In some aspects, each vector further comprises a sequence encoding a fluorescent protein that exhibits different fluorescence.

Also provided, in one embodiment, is a method for determining that a cell produces and secrets a bispecific antibody, wherein the cell has been transfected with a first vector comprising a sequence encoding a first monovalent antigen-binding unit having specificity to a first antigen and a second vector comprising a sequence encoding a second monovalent antigen-binding unit having specificity to a second antigen, the method comprising: (a) contacting the cell with (i) a complex comprising a cell-binding agent and the first antigen and (ii) the second antigen, under conditions allowing the complex to bind to the cell surface, the first antigen to bind to the first antigen-binding unit, and the second antigen to bind to the second antigen-binding unit; and (b) detecting that the second antigen is linked to the cell, thereby determining that the cell produces and secrets a bispecific antibody that comprises the first antigen-binding unit and the second antigen-binding unit.

In some aspects, the second antigen is fluorescent-labeled with a first fluorescent color, and wherein the detection comprising identifying a cellular particle exhibiting the first fluorescent color.

In some aspects, the second antigen is fluorescent-labeled with a first fluorescent color and at least one of the vectors comprises a sequence encoding a fluorescent protein having a second fluorescent color, and wherein the detection comprising identifying a cellular particle exhibiting both the first fluorescent color and the second fluorescent color.

Still, in one embodiment, provided is a method for determining that a cell produces and secrets a bispecific antibody, wherein the cell has been transfected with a first vector comprising a sequence encoding a monovalent antigen-binding, single-chain variable fragment (scFv) having specificity to a first antigen and a second vector comprising a sequence encoding a heavy chain and a light chain both together forming an monovalent antigen-binding unit having specificity to a second antigen, the method comprising: (a) contacting the cell with (i) a complex comprising a cell-binding agent and the first antigen and (ii) an antibody having specificity to the light chain, under conditions allowing the complex to bind to the cell surface, the first antigen to bind to the first antigen-binding unit, and the antibody to bind to the light chain; and (b) detecting that the antibody is linked to the cell, thereby determining that the cell produces and secrets a bispecific antibody that comprises the scFv and the antigen-binding unit having the heavy chain and the light chain.

In some aspects, the antibody is fluorescent-labeled with a first fluorescent color, and wherein the detection comprising identifying a cellular particle exhibiting the first fluorescent color. In some aspects, the antibody is fluorescent-labeled with a first fluorescent color and the first vector further comprises a sequence encoding a fluorescent protein having a second fluorescent color, and wherein the detection comprising identifying a cellular particle exhibiting both the first fluorescent color and the second fluorescent color.

In one embodiment, provided is a method for determining that a cell produces and secrets a bispecific antibody, wherein the cell has been transfected with a first vector comprising a sequence encoding a first monovalent antigen-binding unit having specificity to a first antigen and a second vector comprising a sequence encoding a second monovalent antigen-binding unit having specificity to a second antigen, and wherein the first antigen-binding unit and the second antigen-binding unit can form a bispecific antibody having an Fc fragment, the method comprising: (a) contacting the cell with (i) a complex comprising a cell-binding agent and a protein that specifically binds the Fc fragment, (ii) the first antigen, and (iii) the second antigen, under conditions allowing the complex to bind to the cell surface, the protein to bind to the Fc fragment, the first antigen to bind to the first antigen-binding unit, and the second antigen to bind to the second antigen-binding unit; and (b) detecting that the first antigen and the second antigen are linked to the cell, thereby determining that the cell produces and secrets a bispecific antibody that comprises the first antigen-binding unit and the second antigen-binding unit.

In some aspects, the first antigen is fluorescent-labeled with a first fluorescent color and the second antigen is fluorescent-labeled with a second fluorescent color, and wherein the detection comprising identifying a cellular particle exhibiting both the first fluorescent color and the second fluorescent color.

Also provided, in one embodiment, is a method for determining that a cell produces and secrets a bispecific antibody, wherein the cell has been transfected with a first vector comprising a sequence encoding a monovalent antigen-binding, single-chain variable fragment (scFv) having specificity to a first antigen and a second vector comprising a sequence encoding a heavy chain and a light chain both together forming an monovalent antigen-binding unit having specificity to a second antigen, the method comprising: (a) contacting the cell with (i) a complex comprising a cell-binding agent and a protein that specifically binds the Fc fragment, (ii) the first antigen, and (iii) an antibody having specificity to the light chain, under conditions allowing the complex to bind to the cell surface, the protein to bind to the Fc fragment, the first antigen to bind to the ScFv, and the antibody to bind to the light chain; and (b) detecting that the first antigen and the antibody are linked to the cell, thereby determining that the cell produces and secrets a bispecific antibody that comprises the scFv and the antigen-binding unit having the heavy chain and the light chain.

Advantageous Effects of Invention

Advantageous Effects

In some aspects, the first antigen is fluorescent-labeled with a first fluorescent color and the antibody is fluorescent-labeled with a second fluorescent color, and wherein the detection comprising identifying a cellular particle exhibiting both the first fluorescent color and the second fluorescent color.

BRIEF DESCRIPTION OF DRAWINGS

Description of Drawings

Figure 7:
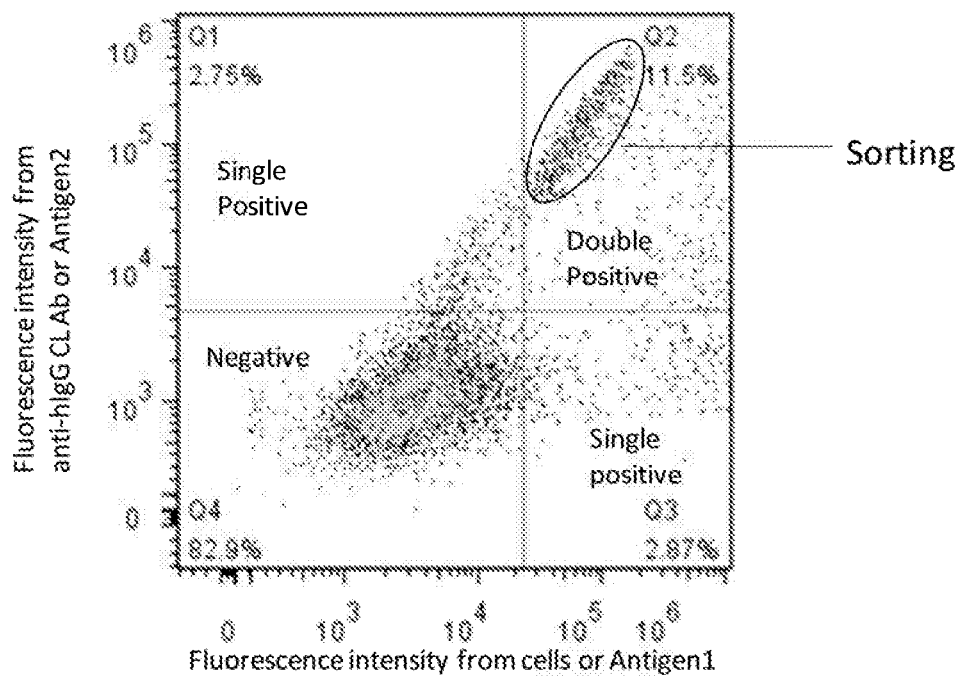
Figure 8:
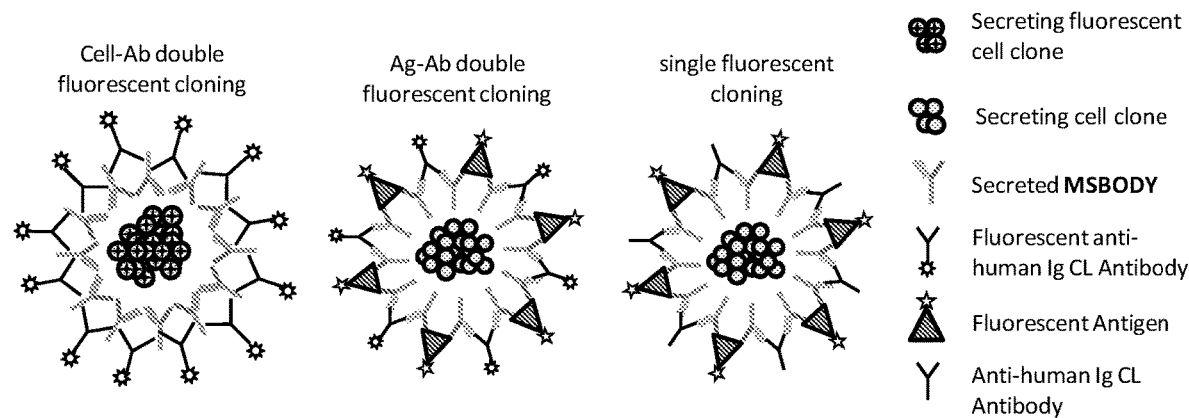
Figure 9:
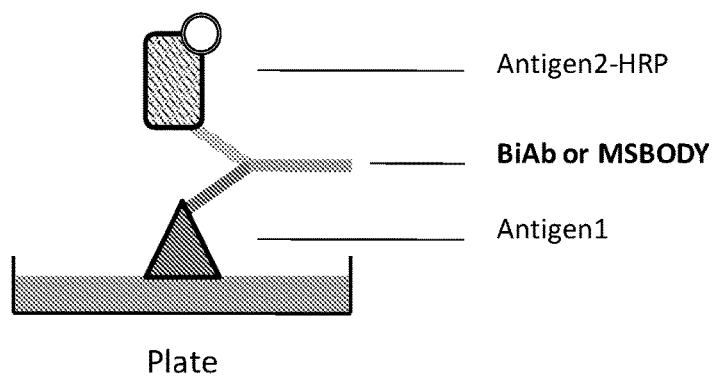
Figure 11:
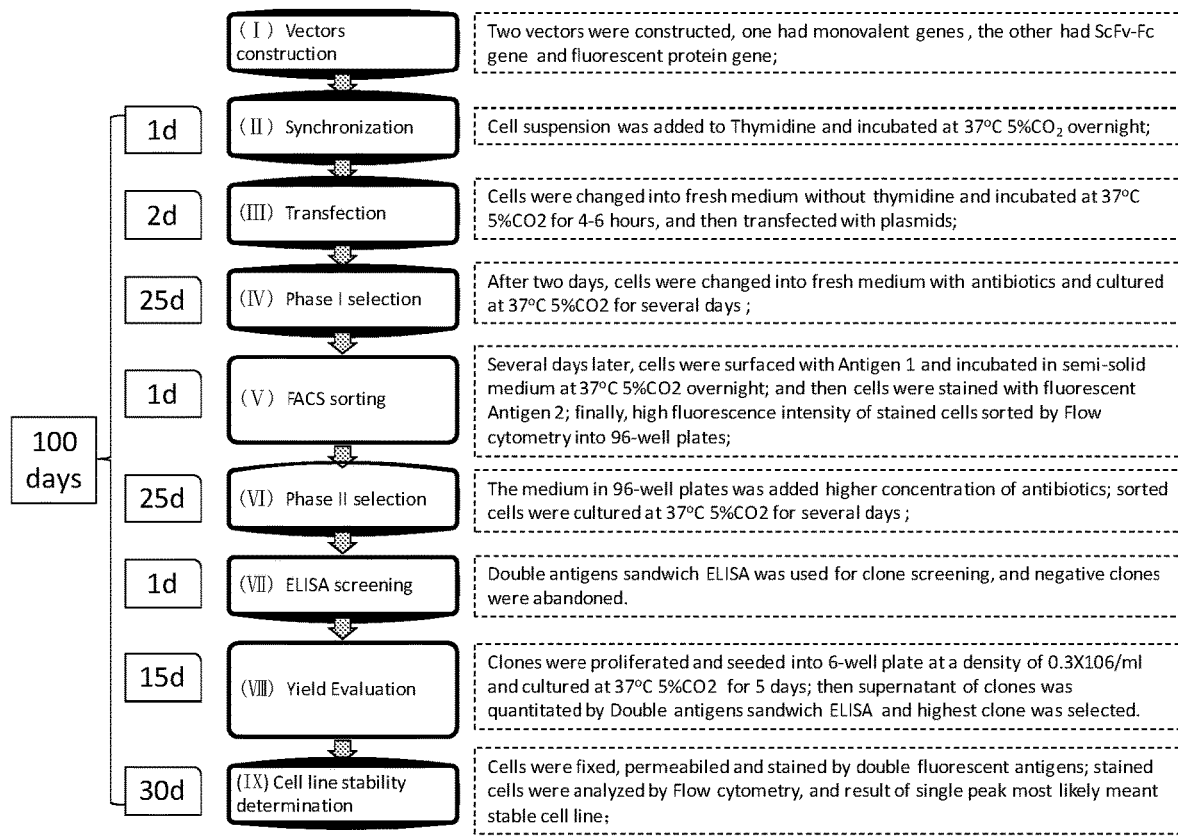
Figure 12:
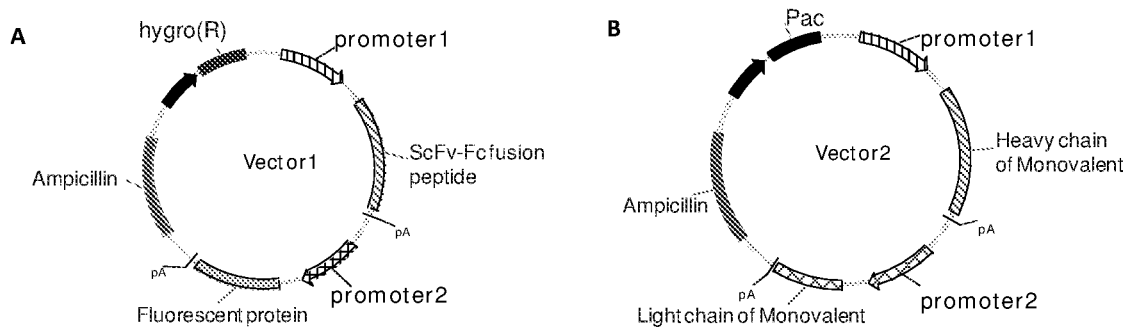
Figure 13:
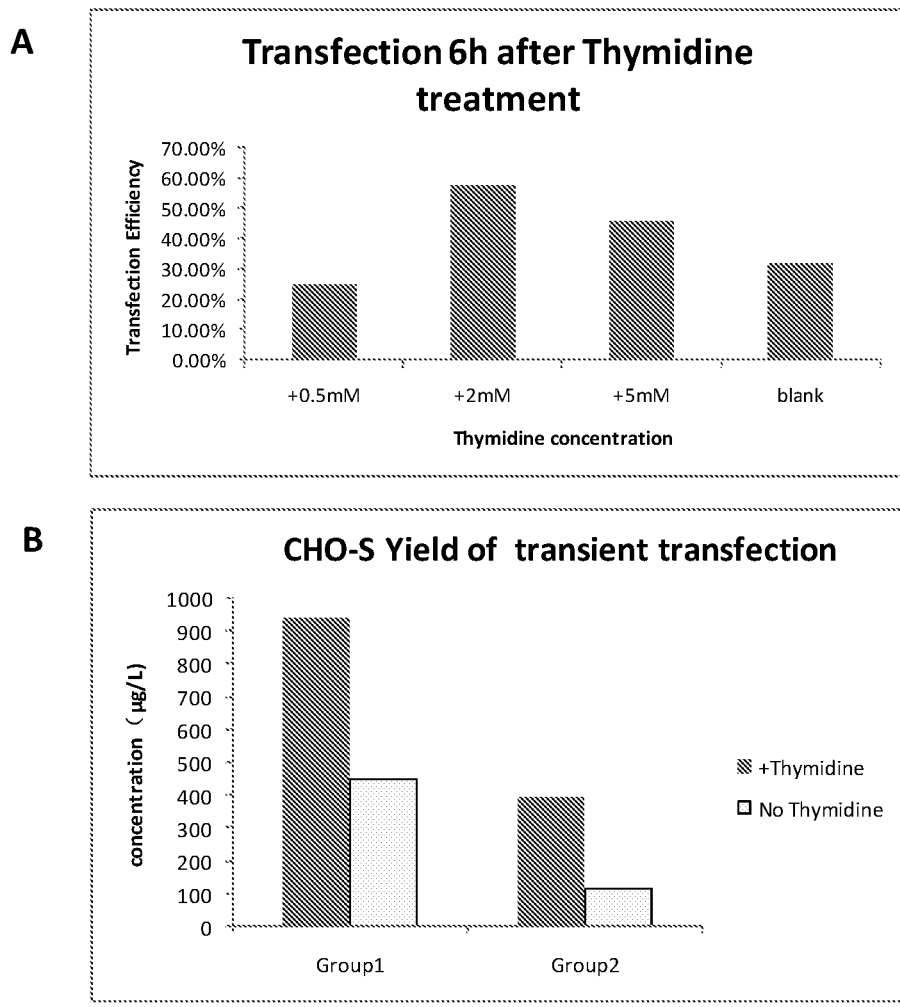

Provided as embodiments of this disclosure are drawings which illustrate by exemplification only, and not limitation, wherein:

FIG. 1 illustrates the general timeline of the conventional cell line development technology and that of one embodiment of the present technology;

FIG. 2-6 show different ways of forming a complex that includes a cell and bispecific antibody the cell secrets for the purpose of screening the cell;

FIG. 7 illustrates how positive cells that express both antigen binding units of the bispecific antibody are sorted;

FIG. 8 illustrates the mechanism of semi-solid medium cloning;

FIG. 9 shows the formation of a dual-antigen/bispecific antibody sandwich for the purpose of quantitating a bispecific antibody;

FIG. 10 A-C illustrate a cell line stability determination method;

FIG. 11 shows a flow chart of the process used in Example 1;

FIG. 12A-B include plasmid maps of two constructs used to express a bispecific antibody;

FIG. 13 A-B compare the transfection efficiency and protein expression with or without cell synchronization; and FIG. 14A-B show correlation between 14-day and 5-day yield evaluation.

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow below.

MODE FOR THE INVENTION

Mode for Invention

Throughout this application, the text refers to various embodiments of the present nutrients, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present disclosure.

Also throughout this disclosure, various publications, patents and published patent specifications are referenced by an identifying citation. The disclosures of these publications, patents and published patent specifications are hereby incorporated by reference into the present disclosure to more fully describe the state of the art to which this present disclosure pertains.

Definitions

As used in the specification and claims, the singular form 'a', 'an' and 'the' include plural references unless the context clearly dictates otherwise. For example, the term 'an electrode' includes a plurality of electrodes, including mixtures thereof.

As used herein, the term 'comprising' is intended to mean that the devices and methods include the recited components or steps, but not excluding others. 'Consisting essentially of' when used to define devices and methods, shall mean excluding other components or steps of any essential significance to the combination. 'Consisting of' shall mean excluding other components or steps. Embodiments defined by each of these transition terms are within the scope of this present disclosure.

All numerical designations, e.g., distance, size, temperature, time, voltage and concentration, including ranges, are approximations which are varied (+) or (−) by increments of 0.1. It is to be understood, although not always explicitly stated that all numerical designations are preceded by the term 'about'. It also is to be understood, although not always explicitly stated, that the components described herein are merely exemplary and that equivalents of such are known in the art.

As used herein, the term 'polypeptide' is intended to encompass a singular 'polypeptide' as well as plural 'polypeptides,' and refers to a molecule composed of monomers (amino acids) linearly linked by amide bonds (also known as peptide bonds). The term 'polypeptide' refers to any chain or chains of two or more amino acids, and does not refer to a specific length of the product. Thus, peptides, dipeptides, tripeptides, oligopeptides, 'protein', 'amino acid chain', or any other term used to refer to a chain or chains of two or more amino acids, are included within the definition of 'polypeptide', and the term 'polypeptide' may be used instead of, or interchangeably with any of these terms. The term 'polypeptide' is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

'Homology' or 'identity' or 'similarity' refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An 'unrelated' or 'non-homologous' sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of 'sequence identity' to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Biologically equivalent polynucleotides are those having the above-noted specified percent homology and encoding a polypeptide having the same or similar biological activity.

The term 'an equivalent nucleic acid or polynucleotide' refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, 'an equivalent polypeptide' refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent sequence retains the activity (e.g., epitope-binding) or structure (e.g., salt-bridge) of the reference sequence.

Hybridization reactions can be performed under conditions of different 'stringency'. In general, a low stringency hybridization reaction is carried out at about 40° C. in about 10× SSC or a solution of equivalent ionic strength/temperature. A moderate stringency hybridization is typically performed at about 50° C. in about 6× SSC, and a high stringency hybridization reaction is generally performed at about 60° C. in about 1× SSC. Hybridization reactions can also be performed under 'physiological conditions' which is well known to one of skill in the art. A non-limiting example of a physiological condition is the temperature, ionic strength, pH and concentration of $Mg^{2+}$ normally found in a cell.

As used herein, the term 'detectable label' intends a directly or indirectly detectable compound or composition that is conjugated directly or indirectly to the composition to be detected, e.g., polynucleotide or protein such as an antibody so as to generate a 'labeled' composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluoresecence assays, the detectable response may be generated directly using a luminophore or fluorophore associated with an assay component actually involved in binding, or indirectly using a luminophore or fluorophore associated with another (e.g., reporter or indicator) component.

As used herein, an 'antibody' or 'antigen-binding polypeptide' refers to a polypeptide or a polypeptide complex that specifically recognizes and binds to an antigen. An antibody can be a whole antibody and any antigen binding fragment or a single chain thereof. Thus the term 'antibody' includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms 'antibody fragment' or 'antigen-binding fragment', as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term 'antibody fragment' includes aptamers, spiegelmers, and diabodies. The term 'antibody fragment' also includes any synthetic or genetically engineered protein that acts like an antibody by binding to a specific antigen to form a complex.

A 'single-chain variable fragment' or 'scFv' refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker ScFv molecules are known in the art and are described, e.g., in U.S. Pat. No. 5,892,019.

The term 'antibody' encompasses various broad classes of polypeptides that can be distinguished biochemically. Those skilled in the art will appreciate that heavy chains are classified as gamma, mu, alpha, delta, or epsilon with some subclasses among them. It is the nature of this chain that determines the 'class' of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a 'Y' configuration wherein the light chains bracket the heavy chains starting at the mouth of the 'Y' and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda. Each heavy chain class may be bound with either a kappa or lambda light chain. In general, the light and heavy chains are covalently bonded to each other, and the 'tail' portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms 'constant' and 'variable' are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VL chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six 'complementarity determining regions' or 'CDRs' present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as 'framework' regions, show less inter-molecular variability. The framework regions largely adopt a n-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see 'Sequences of Proteins of Immunological Interest,' Kabat, E., et al., U.S. Department of Health and Human Services, (1983); and Chothia and Lesk, *J. Mol. Biol.*, 196:901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term 'complementarity determining region' ('CDR') to describe the non-contiguous antigen combining sites found within the variable region of both heavy and light chain polypeptides. This particular region has been described by Kabat et al., U.S. Dept. of Health and Human Services, 'Sequences of Proteins of Immunological Interest' (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term 'heavy chain constant region' includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term 'light chain constant region' includes amino acid sequences derived from antibody light chain. Preferably, the light chain constant region comprises at least one of a constant kappa domain or constant lambda domain.

A 'light chain-heavy chain pair' refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term 'VH domain' includes the amino terminal variable domain of an immunoglobulin heavy chain and the term 'CH1 domain' includes the first (most amino terminal) constant region domain of an immunoglobulin heavy chain. The CH1 domain is adjacent to the VH domain and is amino terminal to the hinge region of an immunoglobulin heavy chain molecule.

As used herein the term 'CH2 domain' includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, 'Sequences of Proteins of Immunological Interest' (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term 'hinge region' includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term 'disulfide bond' includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term 'chimeric antibody' will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

By 'specifically binds' or 'has specificity to,' it is generally meant that an antibody binds to an epitope via its antigen-binding domain, and that the binding entails some complementarity between the antigen-binding domain and the epitope. According to this definition, an antibody is said to 'specifically bind' to an epitope when it binds to that epitope, via its antigen-binding domain more readily than it would bind to a random, unrelated epitope. The term 'specificity' is used herein to qualify the relative affinity by which a certain antibody binds to a certain epitope. For example, antibody 'A' may be deemed to have a higher specificity for a given epitope than antibody 'B,' or antibody 'A' may be said to bind to epitope 'C' with a higher specificity than it has for related epitope 'D.'

As used herein the terms 'fused,' 'linked' and 'conjugated' refer to the linkage between the first antigen binding moiety and the second antigen binding moiety in the bispecific antibody. The linkage may be introduced through either recombinant (e.g. recombinant fusion proteins) or chemical means. Non-limiting examples of suitable chemical means include covalent bonding, disulfide bonding, hydrogen bonding, electrostatic bonding, and conformational bonding and may involve the use of homobifunctional or heterobifunctional cross linkers. Suitable cross-linking and conjugation methods are disclosed in Sen et al. *J. Hemato. Stem Cell Res.* 2001, 10:247-260; U.S. Pat. No. 6,642,363 and US Appl. No. 20060002852.

Cell Line Development

The present disclosure provides compositions and methods for generating and selecting cell lines suitable for bispecific antibody production. In general, the technology is applicable to any bispecific antibody, which includes two different binding domains which target different antigens or epitopes. Certain aspects of the technology, nevertheless, can be particularly suitable for bispecific antibodies in which the two binding domains are on separate peptide chains.

In the conventional antibody production technology, it typically takes 6-8 months to generate and select a suitable cell line. The conventional procedure includes a phase I cell line selection (1 month), a phase II cell line selection (1 month), single clone characterization and production evaluation (0.5 month), stability assessment (1 month), and sub-clone selection (3.5 months). With the present technology, however, a cell line that stably produces a bispecific antibody can be established within about 100 days. The comparison of these timelines is illustrated in FIG. 1. A more detailed flow chart illustrating the present disclosure is provided in FIG. 11.

1. Cell Synchronization and Transfection

It is herein discovered that cell cycle synchronization prior to transfection can greatly increase the transfection efficiency, in particular when two separate nucleotide constructs need to be transfected into the cell (see Example 1 and FIG. 13A). Without being bound by any theory, it is contemplated that synchronized cells help ensure balanced introduction of both constructs, leading to higher yield of corrected paired bispecific antibody product, which is a heterodimer. Further, the particular cell cycle phase, especially after G1/S, is likely favorable to cell transfection and chromosome integration.

Thus, in one embodiment, a population of cells is treated with a cell-cycle arresting agent under conditions allowing the cells to arrest at a particular cell cycle phase. In one aspect, the cells are eukaryotic cells such as yeast cells and mammalian cells (e.g., CHO cells or other human cells). In another aspect, the cells are prokaryotic cells such as *E. coli* cells.

A 'cell-cycle arresting agent' is an agent that is able to arrest cell cycle at a particular phase. There are many known cell-cycle arresting agents, including many available commercially, such as thymidine, methotrexate, and hydroxyurea. In a particular embodiment, the cell-cycle arresting agent is thymidine.

In one aspect, the incubation is carried out at about room temperature for 8 to 24 hours with about 5% $CO_2$. The incubation condition, however, can be tweaked for each agent and cell line. In one aspect, thymidine is used and the concentration of thymidine is from about 0.5 mM to about 5 mM. In one aspect, the concentration of thymidine is at least about 0.5 mM, 0.6 nM, 0.7 mM, 0.8 mM, 0.9 mM, 1 mM, 1.5 mM, 2 mM, 2.5 mM, 3 mM or 4 mM. In another aspect, the concentration of thymidine is not higher than about 5 mM, 4.5 mM, 4 mM, 3.5 mM, 3 mM, 2.5 mM, or 2 mM.

Different agents may inhibit cell cycle at different phases, but nevertheless can achieve the same synchronization results. For instance, if an agent arrests cells at phase G1, the cells can be allowed to grow, after the agent is removed, to phase G2, M, or S. Still, after the cells are at the same phase, achieving the synchronization goal. In one aspect, following removal of the cell-cycle arresting agent, the cells are incubated for at least two hours prior to transfection. In another aspect, the cells are incubated for at least about 3, 4, 5, 6, 7, 8, 9, 10 or 12 hours. In another aspect, the incubation is not longer than about 18, 16, 15, 14, 13, 12, 10, 9, 8, 7, 6, 5, or 4 hours.

The synchronized cells, e.g., at G1/S, G2 or M phase, are then incubated with nucleotide constructs to initiate transfection. In some aspects, at least two separate constructs are used, each encoding a separate antigen-binding unit. In one aspect, each construct includes an antibiotic resistant gene allowing antibiotic-based cell selection (Phase I selection).

2. Bispecific Antibody Identification on Cell Surface

Following antibiotic-based Phase I cell selection, the cells can then be screened for actual expression and secretion of bispecific antibodies. In one aspect, the cells are incubated in a medium with a complex that is able to bind to the cell as well as the antibody.

FIG. 2-6 illustrate different ways a cell is identified for producing and secreting a desired bispecific antibody. With reference to FIG. 2, a cell (1) is incubated with a complex (annotated as 2, 'B-N-A complex'). The complex includes a unit that is able to bind to the cell (a 'cell-binding unit') and a unit that can bind to the bispecific antibody.

A 'cell-binding unit' refers to a molecule or moiety that is capable of binding to a cell, such as by binding to a cell surface receptor or cell membrane protein. For instance, a cell-binding unit can be an antibody recognizing a cell membrane protein or a ligand that binds to a cell surface receptor. As illustrated in FIG. 2, the cell-binding unit is Concanavalin A (Con A). Con A (or Succinyl-Con A) non-specifically binds to cell surface through glycosyl of membrane surface glycoprotein.

The complex further includes a unit that binds to the bispecific antibody. As illustrated in FIG. 2, this unit is one of the antigens (Antigen 1) that the bispecific antibody targets.

The two binding units are held together in the complex by two biotins and a neutravidin which binds to the biotins. Therefore, once in contact with the cell, the complex is able to bind to the cell through the cell-binding unit/cell membrane connection. Meanwhile, if the cell secrets the bispecific antibody (3), the complex will also bind the antibody, forming a cell-complex-antibody complex.

By virtue of the dual specificity of the antibody, such a cell-complex-antibody can be readily detected by binding to the second antigen (Antigen 2) of the antibody, in particular when Antigen 2 is labeled with a fluorescent dye (FIG. 2). In some embodiments, at least one of the constructs transfected to the cell further encodes a fluorescent protein such that the cell itself is fluorescent-labeled. In some aspects, the cell and Antigen 2 exhibit different fluorescence so that a dual staining further confirms the formation of the large complex that includes both the cell and the bispecific antibody.

The presence of fluorescence within the cell, however, is not necessary. As shown in FIG. 3, the large complex that includes the cell, the bispecific antibody and both antigens can be readily recognized by the fluorescent on Antigen 2 as well as the large size of the complex, for instance.

In some aspects, the bispecific antibody is a monovalent and single-chain antibody (MSBODY), which includes a light chain-heavy chain pair from a full antibody having a first specificity, coupled to a single-chain unit (scFv) having a second specificity. More description of MSBODY can be found in PCT/CN2012/084982, the content of which is incorporated to the present disclosure by reference. For such a particular bispecific antibody, the detection method as illustrated in FIG. 4A-B can be also used.

In FIG. 4A, the same B-N-A complex can be used as in FIG. 2. Different from Antigen 2, however, an antibody that recognizes the immunoglobulin (Ig) light chain can be used, provided that the scFv unit of the antibody is specific to Antigen 1. Further, in FIG. 4B, it can be readily appreciated that the anti-light chain antibody can replace Antigen 1 in the complex (referred to as B-N-B complex), while Antigen 1 can be stand alone, optionally labeled with a fluorescent dye. Also, in one aspect, the cell can be fluorescence-free or labeled with a fluorescent protein encoded by one of the constructs.

Figure 4:
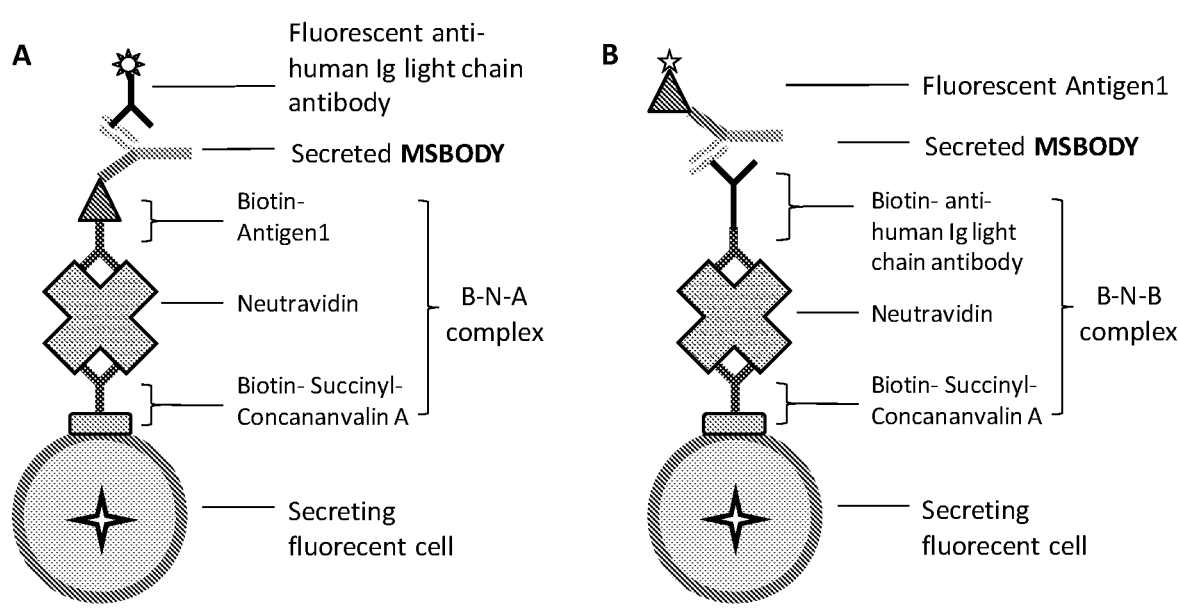
Figures 5, 6:
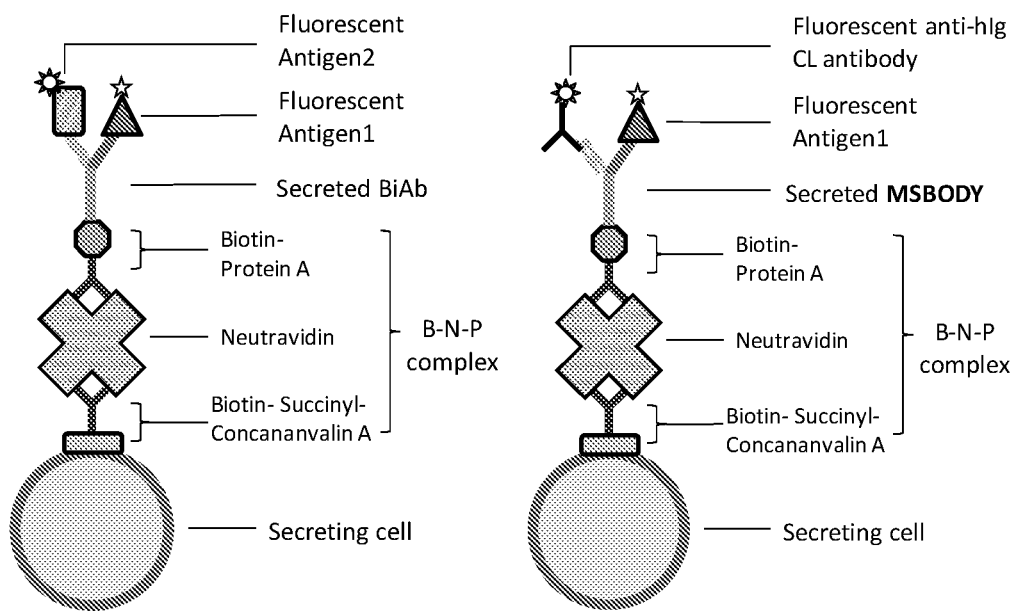

In some embodiments, the complex that binds both the cell and the bispecific antibody can take another form, as illustrated in FIGS. 5 and 6. For instance, as shown in FIG. 5, the complex (referred to as a B-N-P complex) includes a cell-binding unit connected to an Fc-binding unit. The 'Fc-binding unit' is any molecule or moiety that can bind to the Fc fragment of an immunoglobulin. Examples of such binding molecules are well known in the art, such as Protein A, which is a 56 kDa surface protein originally found in the cell wall of the bacterium *Staphylococcus aureus*. Protein A is encoded by the spa gene and binds to the Fc fragment of immunoglobulins. As shown in FIG. 6, the 'anti-hIg CL Ab' is an anti-human Ig light chain constant region antibody.

The B-N-P complex is able to bind to both the cell and the bispecific antibody. To detect confirm such binding, both antigens (Antigen 1 and Antigen 2) that the antibody targets can be added to the incubation. In some aspects, at least one of the antigens is labeled with a fluorescent dye. In some aspects, both antigens are labeled, preferable with dyes of different colors (FIG. 5).

Alternatively, for a MSBODY, rather than using both antigens, the complex can be detected with an antibody that recognizes the light chain and an antigen that the scFv recognizes (FIG. 6).

In some of the above embodiments, the final complex is a cell labeled with a fluorescent dye or two different fluorescent dyes. These complexes can be sorted out using these dyes. For instance, with two different dyes, FIG. 7 illustrates a FACS (fluorescence-activated cell sorting) mechanism, in which the double-positive complexes are sorted and collected.

The above experiments can be carried out in a regular cell culture medium. In some aspects, the incubation and detection is carried out in a semi-solid medium which may be useful as it restricts the movement of cells and can facilitate formation of complexes. Alternatively, if the cells, complexes and the antigens are incubated in a semi-solid medium, clones, rather the single cells, can be selected for further culturing.

FIG. 8 illustrates such a clone selection process in a semi-solid medium. The complexes and antigens or antibodies are as explained above for FIG. 2-7. A semi-solid medium can be prepared by, for instance, adding 1% methylcellulose into a basic medium.

The left panel of FIG. 8 illustrates Cell-Ab double fluorescent cloning. Cells are fluorescent labeled and incubated in a semi-solid medium (Basic medium+1% Methylcellulose) together with a fluorescent anti-human Ig CL antibody so that the right clones are double fluorescent. Clones with high intensity of both fluorescence are picked to 96-well plate for Phase II selection.

In the middle panel, antigen (Ag)-antibody (Ab) double fluorescent clones are selected. Fluorescent Ag and fluorescent anti-human Ig CL Ab are added into basic medium in 1% Methylcellulose. Double fluorescence can be observed if one clone secreted MSBODY. Those clones are picked to 96-well plate for Phase II selection.

The right panel shows single fluorescent cloning. There, anti-human Ig CL Ab and Fluorescent Ag are added into semi-solid medium (Basic medium+1% Methylcellulose). Clones with high fluorescent intensity are picked to 96-well plate for Phase II selection.

3. Phase II Selection and ELISA Screening

Selected cells or cell clones can then be subjected to Phase II selection. For instance, each of the cells or clones is placed in a well on a 96-well format. Antibiotics, in particular at a concentration higher than what is used in Phase I, can be used to select cells.

Following Phase II selection, the cells can be further validated with an ELISA-based screen, which is described in more detail below. Each sample from the 96-well plate can be optionally processed to remove the cells in the medium. Then, the sample is placed on a scaffold (such as a plate, a well or a bead) which is coated with a first antigen (Antigen 1) that the bispecific antibody targets.

Once the bispecific antibody is in contact with Antigen 1, it will bind to Antigen 1 and be immobilized on the scaffold (FIG. 9). Meanwhile, if the other target of the bispecific antibody, Antigen 2, is also present in the solution, the bispecific antibody will bind to Antigen 2 as well, forming a scaffold-Antigen 1-bispecific antibody-Antigen 2 complex. Such a complex and readily detected and quantitated by, for instance, conjugating a signal amplifier (e.g., a horseradish peroxidase, or HRP).

Such an antibody quantitation method is generally applicable to any bispecific antibodies. The method is quick, accurate and cost-effective as it does not even require any antibodies or secondary antibodies.

Thus, provided in one embodiment is a method for detecting or measuring a bispecific antibody having specificity to a first antigen and a second antigen. The method entails contacting a sample containing the bispecific antibody with a first antigen and a second antigen under conditions allowing the first and second antigens to bind to the antibody. In one aspect, at least one of the antigens is attached or immobilized to a solid support, such as a plate, a well or a bead. In one aspect, the other antigen comprises a detectable label.

In one aspect, the detectable label is a fluorescent dye. In another aspect, the detectable label reacts with an agent to generate fluorescence.

4. Yield Evaluation and Stability Determination

Based on the quantitation of secreted bispecific antibody and the culture conditions and time, a yield evaluation can be performed, as illustrated in Example 1 and FIG. 14A-B.

Figure 10A:
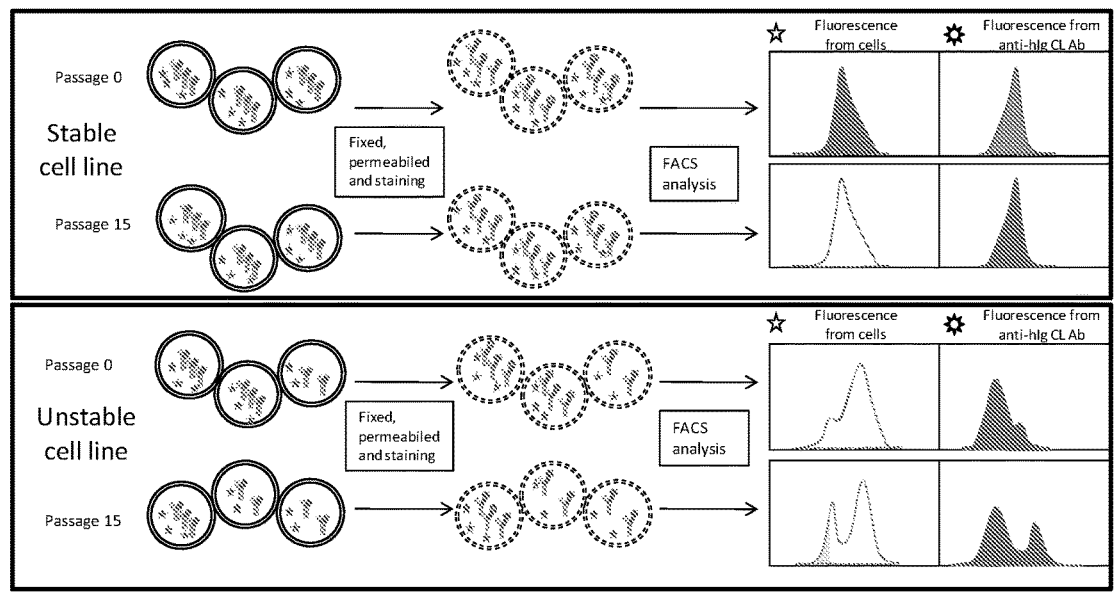

To determine the stability of the selected cell line, the cells can be fixed, permeabilized and stained with anti-hIg CL antibody (see, e.g., FIG. 2-6) labeled with fluorescence which is different from cell inner fluorescence. The stained cells can then be analyzed by flow cytometry. FIG. 10A shows the two representative flow cytometry spectra, which can be used to ascertain the stability of the cell lines. In the upper panel, after 15 passages, the flow cytometry show the same single peaks, indicating that this cell line is stable. By contrast, in the lower panel, all flow cytometry spectra exhibit two of more peaks and some of the peaks also shift after the passages. These are indication of an unstable cell line.

In some embodiments, the present disclosure provides kits comprising the compositions of, and instructions for use.

EXPERIMENTAL EXAMPLES

Example 1. Generation, Selection and Evaluation of a Stable Cell Line Producing a Bispecific Antibody This experiment followed the process illustrated in the flow chart of FIG. 11. Two plasmids of which both had dual promoter were constructed each encoding a binding unit of a bispecific antibody. FIG. 12A presents the map of a single-chain unit (a scFv-Fc fusion peptide) of the bispecific antibody. In addition to the scFv-Fc fusion peptide, the plasmid also includes a sequence encoding a red fluorescent protein (RFP) and an antibiotic-resistant gene (hygromycin).

The plasmid in FIG. 12B encodes both the light chain and heavy chain of the monovalent unit of the bispecific antibody. Here, no fluorescent protein sequence is present but this plasmid also includes an antibiotic-resistant genes (puromycin). The use of double resistance helped to ensure two plasmid s integration.

At step II, thymidine was added to the cell suspension (CHO cells) and incubated at 37° C., with 5% $CO_2$ overnight. The concentration of thymidine was 2 mM but could vary between 0.5 mM to 5 mM. Thymidine was removed, and the cells were allowed to grow for 6 hr, before transfection was performed. The cells were synchronized at the G1/S phase before transfection.

Double antibody ELISA was used for quantification two days following transfection.

As shown in FIG. 13B, the yield of thymidine-treated groups was significantly higher than that of untreated groups, indicating that cell cycle synchronization was helpful in improving the transfection efficiency (FIG. 13A). Here, group 1 and group 2 were expressing different bispecific antibodies.

Two days following the transfection, cells were changed into fresh medium with Hygromycin and Puromycin and cultured at 37° C. 5% $CO_2$ for several days, undergoing Phase I antibiotic selection.

Two weeks later, cells were surfaced with Antigen 1 and incubated in semi-solid medium at 37° C. 5% $CO_2$ overnight; and then the cells were stained with FITC conjugated Antigen 2. Next, double positive cells (RFP and FITC) were sorted by flow cytometry into 96-well plates, followed by a Phase II antibiotic selection with higher concentrations of the antibiotics. Sorted cells were then cultured at 37° C. 5% $CO_2$ for two weeks.

Double-antigen sandwich ELISA (FIG. 9) was used for clone screening, and negative clones were abandoned.

Clones were proliferated and seeded into 6-well plate at a density of $0.3 \times 10^6$/ml and cultured at 37° C. 5% $CO_2$ for 5 days. Supernatant of clones was quantitated by double-antigens sandwich ELISA and positive clone s w ere selected.

Conventionally, yield evaluation is carried out 14 days following proliferation. As FIG. 14A-B show, however, there was good correlation between the yield at $14^{th}$ day and that at the $5^{th}$ day. Accordingly, it is herein discovered that a 5-day evaluation is adequate for the purpose of evaluating the yield of a cell line. This can shorten the timeline for cell line development.

Figure 10B:
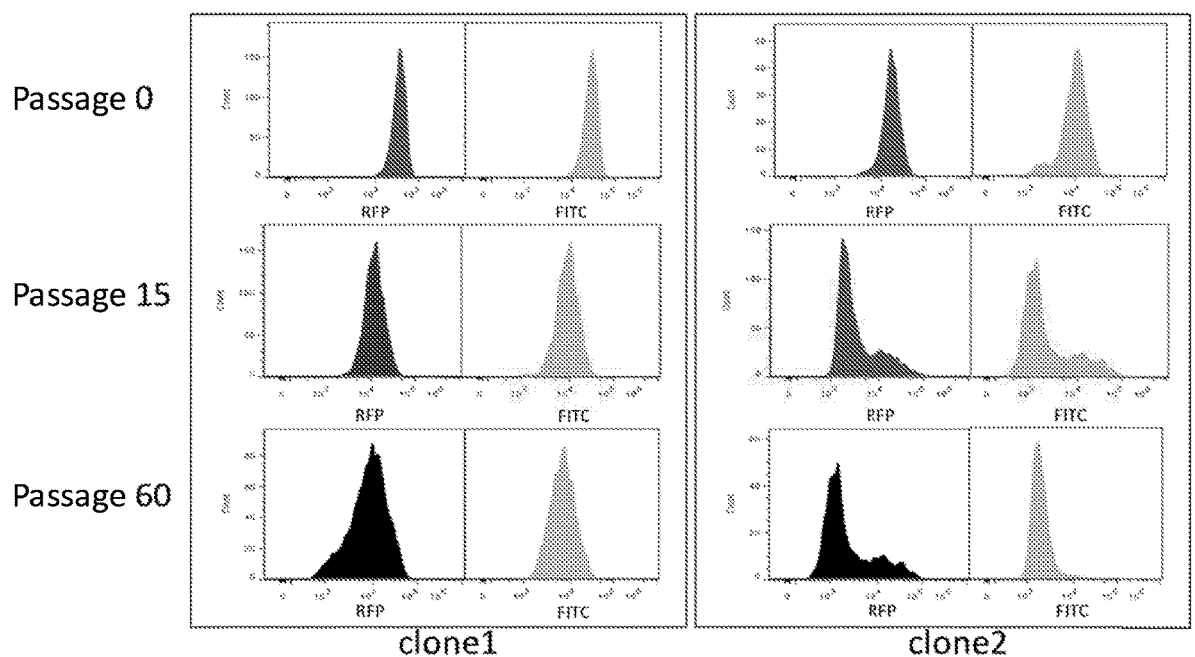

To determine the stability of the cell lines, the cells were fixed, permeabilized and stained by FITC conjugated anti-hCL antibody. The stained cells were analyzed by flow cytometry according to two fluorescence channels involved RFP and FITC, in both of which single peak indicated stable cell line (FIG. 10B).

Figure 10C:
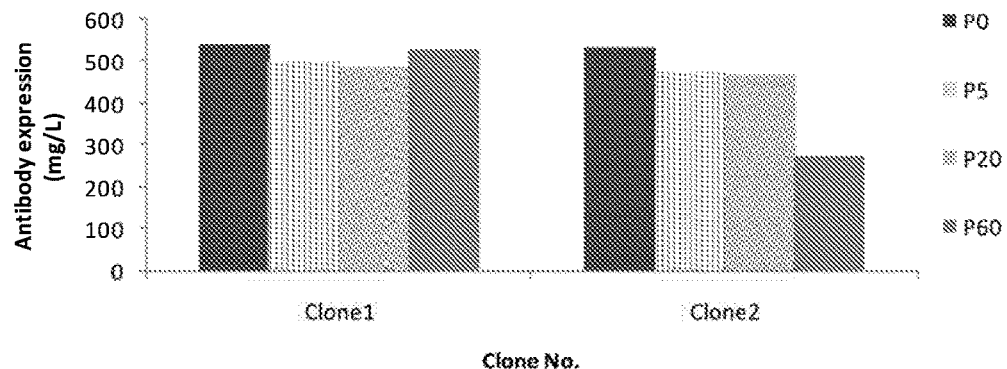

In the conventional technology, cells are cultured continuously for 60 passages, and then the 14-d yield between primary cells and cells of 60 passages were compared (FIG. 10C). If the yield reduction is less than 20%, then the cell line is considered stable. In FIG. 10C, according to the result of yield evaluation of 60 passages, Clone1 was stable, and Clone2 was unstable. Here, with the staining and the improved transfection method, cell line stability could be evaluated after just 15 passages (FIG. 10B).

It is to be understood that while the present disclosure has been described in conjunction with the above embodiments, that the foregoing description and examples are intended to illustrate and not limit the scope of the present disclosure. Other aspects, advantages and modifications within the scope of the present disclosure will be apparent to those skilled in the art to which the present disclosure pertains.

The present disclosure is not to be limited in scope by the specific embodiments described which are intended as single illustrations of individual aspects of the present disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

The invention claimed is:

1. A method for determining that a cell produces and secrets a bispecific antibody, wherein the cell has been transfected with a first vector comprising a sequence encoding a monovalent antigen-binding, single-chain variable fragment (scFv) having specificity to a first antigen and a second vector comprising a sequence encoding a heavy chain and a light chain both together forming a monovalent antigen-binding unit having specificity to a second antigen, the method comprising:
   contacting the transfected cell with (i) a complex comprising a cell-binding agent capable of binding to the surface of the transfected cell and the first antigen and (ii) an antibody having specificity to the light chain, to allow the complex to bind to the cell surface via the cell-binding agent, the first antigen to bind to the scFv, the antibody to bind to the light chain, and the light chain to bind to the heavy chain; and
   detecting that the antibody is linked to the transfected cell, thereby determining that the antibody binds to the light chain, which binds to the heavy chain, which binds to the scFv, which binds to the first antigen in the complex, which complex binds to the surface of the transfected cell, indicating that the transfected cell produces and secrets a bispecific antibody that comprises the scFv and the antigen-binding unit having the heavy chain and the light chain.

2. The method of claim 1, wherein the antibody is fluorescent-labeled with a first fluorescent color.

3. The method of claim 2, wherein the antibody is fluorescent-labeled with a first fluorescent color and the first vector further comprises a sequence encoding a fluorescent protein having a second fluorescent color.

4. A method for determining that a cell produces and secrets a bispecific antibody, wherein the cell has been transfected with a first vector comprising a sequence encoding a monovalent antigen-binding, single-chain variable fragment (scFv) having specificity to a first antigen and a second vector comprising a sequence encoding a heavy chain and a light chain both together forming monovalent antigen-binding unit having specificity to a second antigen, the method comprising:

contacting the transfected cell with (i) a complex comprising a cell-binding agent capable of binding to the surface of the transfected cell and an antibody having specificity to the light chain and (ii) the first antigen, to allow the complex to bind to the cell surface via the cell-binding agent, the first antigen to bind to the scFv, and antibody to bind to the light chain and the light chain to the heavy chain; and detecting that the first antigen is linked to the transfected cell, thereby determining that the first antigen binds to the scFv, which binds to the heavy chain, which binds to the light chain, which binds to the antibody in the complex, which complex binds to the surface of the transfected cell, indicating that the transfected cell produces and secrets a bispecific antibody that comprises the scFv and the antigen-binding unit having the heavy chain and the light chain.

5. The method of claim 4, wherein the first antigen is fluorescent-labeled with a first fluorescent color.

6. The method of claim 5, wherein the first antigen is fluorescent-labeled with a first fluorescent color and the first vector further comprises a sequence encoding a fluorescent protein having a second fluorescent color.

* * * * *